(12) United States Patent
Aoyagi et al.

(10) Patent No.: US 10,413,236 B2
(45) Date of Patent: Sep. 17, 2019

(54) MEDICAL-IMAGE PROCESSING APPARATUS

(71) Applicants: Toshiba Medical Systems Corporation, Otawara-shi (JP); National University Corporation Kobe University, Kobe-shi (JP)

(72) Inventors: Kota Aoyagi, Nasushiobara (JP); Hitoshi Yamagata, Otawara (JP); Mizuho Nishio, Kobe (JP); Sumiaki Matsumoto, Kobe (JP)

(73) Assignees: Canon Medical Systems Corporation, Otawara-shi (JP); NATIONAL UNIVERSITY CORPORATION KOBE UNIVERSITY, Kobe-shi (JP)

( * ) Notice: Subject to any disclaimer, the term of this patent is extended or adjusted under 35 U.S.C. 154(b) by 419 days.

(21) Appl. No.: 14/747,199

(22) Filed: Jun. 23, 2015

(65) Prior Publication Data

US 2015/0366500 A1    Dec. 24, 2015

(30) Foreign Application Priority Data

Jun. 23, 2014   (JP) .................................. 2014-128462

(51) Int. Cl.
*A61B 5/00*         (2006.01)
*G06T 7/00*         (2017.01)
(Continued)

(52) U.S. Cl.
CPC .......... *A61B 5/4842* (2013.01); *A61B 5/7485* (2013.01); *A61B 90/37* (2016.02);
(Continued)

(58) Field of Classification Search
CPC ..... A61B 5/4842; A61B 5/7485; A61B 90/37; G06T 7/0012
See application file for complete search history.

(56) References Cited

U.S. PATENT DOCUMENTS 5,857,030 A * 1/1999 Gaborski ................. G06K 9/62
378/37
6,549,646 B1 * 4/2003 Yeh ...................... G06K 9/6814
382/132
(Continued)

FOREIGN PATENT DOCUMENTS

JP    2004-532067 A    10/2004
JP    2009-028161 A     2/2009
(Continued)

OTHER PUBLICATIONS

Office Action dated Apr. 3, 2018, in Japanese Patent Application No. 2014-128462, filed Jun. 23, 2014, 137 pages.

*Primary Examiner* — Tse W Chen
*Assistant Examiner* — Joanne M Hoffman
(74) *Attorney, Agent, or Firm* — Oblon, McClelland, Maier & Neustadt, L.L.P.

(57) ABSTRACT

A medical-image processing apparatus according to an embodiment includes an extracting unit, a dividing unit, and an estimating unit. The extracting unit extracts a disease candidate region from a medical image. The dividing unit divides the disease candidate region into multiple partial regions. The estimating unit uses the feature value of each of the partial regions to estimate the disease state of the disease candidate region.

3 Claims, 7 Drawing Sheets

(51) Int. Cl.
*A61B 90/00* (2016.01)
*A61B 5/055* (2006.01)
*G06F 19/00* (2018.01)

(52) U.S. Cl.
CPC .......... *G06T 7/0012* (2013.01); *A61B 5/0013* (2013.01); *A61B 5/055* (2013.01); *A61B 5/7264* (2013.01); *A61B 2090/374* (2016.02); *A61B 2090/378* (2016.02); *A61B 2090/3762* (2016.02); *A61B 2576/00* (2013.01); *G06F 19/321* (2013.01); *G06T 2207/10081* (2013.01); *G06T 2207/10088* (2013.01); *G06T 2207/10116* (2013.01); *G06T 2207/10132* (2013.01); *G06T 2207/30064* (2013.01); *G06T 2207/30096* (2013.01)

(56) References Cited

U.S. PATENT DOCUMENTS

| | | | | |
|---|---|---|---|---|
| 7,177,458 | B1* | 2/2007 | Savareigo | G01N 21/956 250/559.45 |
| 2002/0165837 | A1* | 11/2002 | Zhang | G06K 9/623 706/16 |
| 2002/0192686 | A1* | 12/2002 | Adorjan | C12Q 1/6883 435/6.12 |
| 2005/0171409 | A1* | 8/2005 | Arimura | G06T 7/0012 600/300 |
| 2007/0036406 | A1* | 2/2007 | Bogoni | G06T 7/0012 382/128 |
| 2007/0230763 | A1* | 10/2007 | Matsumoto | G06T 7/0012 382/131 |
| 2007/0274583 | A1* | 11/2007 | Sugiyama | G06T 15/08 382/131 |
| 2008/0040083 | A1* | 2/2008 | Odry | G06T 7/0012 703/2 |
| 2008/0292194 | A1* | 11/2008 | Schmidt | G06T 7/0012 382/217 |
| 2010/0106002 | A1* | 4/2010 | Sugiyama | A61B 5/055 600/410 |
| 2010/0119128 | A1* | 5/2010 | Zhang | G06K 9/6229 382/128 |
| 2010/0208205 | A1* | 8/2010 | Tseng | A61B 3/113 351/209 |
| 2011/0142301 | A1* | 6/2011 | Boroczky | G06T 7/0012 382/128 |
| 2012/0070055 | A1* | 3/2012 | Liu | G06T 7/0016 382/131 |
| 2012/0250966 | A1* | 10/2012 | Fujisawa | G06T 7/0016 382/131 |
| 2015/0078641 | A1* | 3/2015 | Tan | G06T 7/0012 382/131 |
| 2015/0254842 | A1* | 9/2015 | Brown | G06T 7/136 382/131 |
| 2015/0356730 | A1* | 12/2015 | Grove | G01N 23/046 382/124 |

FOREIGN PATENT DOCUMENTS

| | | |
|---|---|---|
| JP | 2009-273771 A | 11/2009 |
| JP | 2012-213604 | 11/2012 |

* cited by examiner

FIG.5
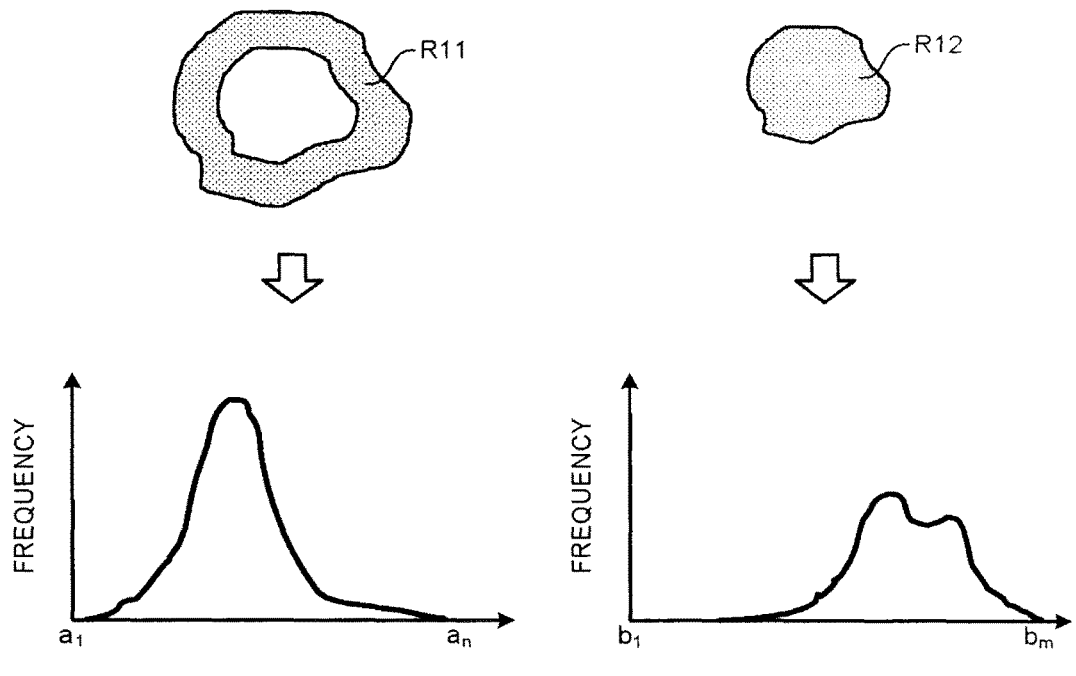
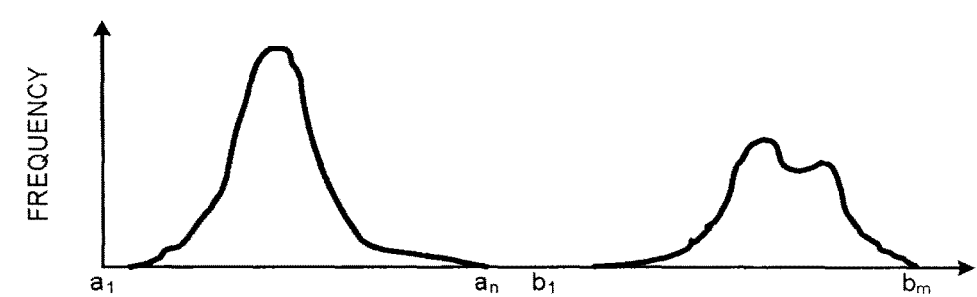

MEDICAL-IMAGE PROCESSING APPARATUS

CROSS-REFERENCE TO RELATED APPLICATIONS

This application is based upon and claims the benefit of priority from Japanese Patent Application No. 2014-128462, filed on Jun. 23, 2014, the entire contents of all of which are incorporated herein by reference.

FIELD

Embodiments described herein relate generally to a medical-image processing apparatus.

BACKGROUND

Various types of image inspections, such as computed tomography (CT), magnetic resonance imaging (MRI), radio isotope (RI), positron emission tomography (PET), or echoes, are conventionally conducted to detect abnormality inside a living organism and examine the cause thereof. During such an image inspection, it is extremely important to, as well as detecting the abnormality inside a living organism, estimate what kind of disease state causes the detected abnormality.

During the above image inspection, doctors often make a visual assessment; however, due to the recent improvements in software technology, assessments are made by image processing using a computer. As a part of the above, intensive studies are carried out on computer-aided diagnoses for image inspections. There are various types of computer-aided diagnoses; however, computer-aided diagnoses are here defined as estimations of the disease state with regard to detected abnormality by using software.

Doctor's visual assessments of image inspections involve human elements, and the assessments are varied and they are not always specific due to doctor's experiences, specialized field, or the like. Therefore, doctors use computer-aided diagnoses during assessments of image inspections so that it is expected that variations of visual assessments are reduced and the diagnosis performance is improved and equalized.

BRIEF DESCRIPTION OF THE DRAWINGS

FIG. 5 is a diagram that illustrates an example of the operation performed by the extracting unit to extract a feature vector according to the first embodiment;

DETAILED DESCRIPTION

According to an embodiment, a medical-image processing apparatus includes processing circuitry. The processing circuitry configured to extract a disease candidate region from a medical image. The processing circuitry configured to divide the disease candidate region into multiple partial regions. The processing circuitry configured to estimate a disease state of the disease candidate region by using a feature value of each of the partial regions.

First Embodiment

Figure 1:
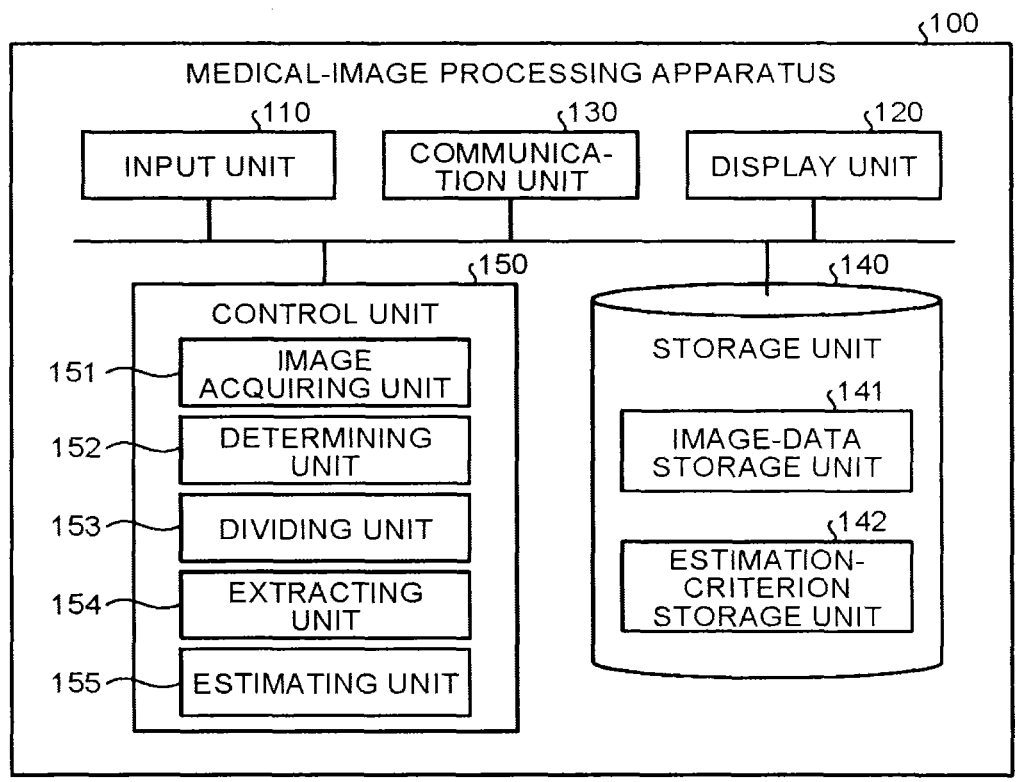
FIG. 1 is a diagram that illustrates an example of the configuration of a medical-image processing apparatus according to a first embodiment.

FIG. 1 is a diagram that illustrates an example of the configuration of a medical-image processing apparatus 100 according to a first embodiment. As illustrated in FIG. 1, the medical-image processing apparatus 100 includes an input unit 110, a display unit 120, a communication unit 130, a storage unit 140, and a control unit 150. For example, the medical-image processing apparatus 100 is a workstation, an arbitrary personal computer, or the like, and it is connected to an undepicted medical-image diagnostic apparatus, an image storage apparatus, or the like, via a network. The medical-image diagnostic apparatus is, for example, an X-ray computed tomography (CT) apparatus, a magnetic resonance imaging (MRI) apparatus, an X-ray diagnostic apparatus, an ultrasonic diagnostic apparatus, or the like. The medical-image diagnostic apparatus generates medical image data. The image storage apparatus is the database that stores medical images. Specifically, the image storage apparatus stores, in a storage unit, the medical image data that is transmitted from the medical-image diagnostic apparatus and keeps it.

The above-described medical-image processing apparatus 100, the medical-image diagnostic apparatus, and the image storage apparatus are in a state such that they can communicate with one another directly or indirectly via, for example, an in-hospital local area network (LAN) that is installed within a hospital. For example, if the picture archiving and communication system (PACS) is introduced, the apparatuses transmit and receive medical images, or the like, to and from one another in accordance with the Digital Imaging and Communications in Medicine (DICOM) format.

The medical-image processing apparatus 100 according to the first embodiment makes it possible to improve the diagnosis performance of computer-aided diagnoses on medical image data that is generated by the medical-image diagnostic apparatus. Here, an explanation is first given of computer-aided diagnoses in conventional technologies. During computer-aided diagnoses in the conventional technologies, the following operation is usually performed to estimate the disease state of the target disease. During the conventional computer-aided diagnosis, (1) the region (disease candidate region) that is the object for an estimation is first determined, (2) a feature vector is extracted from the determined region, and (3) an estimation is made with regard to the extracted feature vector by using machine learning. Furthermore, an estimation criterion is necessary for making an estimation, and the estimation criterion can be generated by applying machine learning to training data (supervised image). It is necessary to previously generate an estimation criterion before making an estimation on unknown data for which the result is unpredictable.

Here, the performance of the machine learning in (3) for making the final output depends on the results of determination of the region in (1) and of extraction of the feature vector in (2); therefore, there is a requirement for the effective techniques for (1) and (2) of the computer-aided diagnosis. Heretofore, various techniques have been proposed for extraction of feature vectors of (2) in the typical computer vision field, and applications to computer-aided diagnoses have been also proposed. However, there are few examples of consideration as to the technique of a combination of two processes, i.e., determination of a region in (1) and extraction of a feature vector in (2), and there is a certain limit on the diagnosis performance of computer-aided diagnoses. For example, the performance of computer-aided diagnoses for benign/malignant differentiation of a lung nodule (determination as to whether the target disease is a malignant tumor) is short of a sufficient level. Thus, the object of the present application is to provide the medical-image processing apparatus 100 for improving the diagnosis performance of computer-aided diagnoses.

With reference back to FIG. 1, the input unit 110 is a mouse, keyboard, trackball, or the like, and it receives, from an operator, various operation inputs on the medical-image processing apparatus 100. For example, the input unit 110 receives inputs of information, or the like, for acquiring medical image data that is the subject for a computer-aided diagnosis from the medical-image diagnostic apparatus or the image storage apparatus. Furthermore, for example, the input unit 110 receives various inputs related to machine learning. Moreover, the input unit 110 receives input operations for setting a disease candidate region for the computer-aided diagnosis.

The display unit 120 is a liquid crystal panel, or the like, and it displays various types of information. Specifically, the display unit 120 displays a graphical user interface (GUI) for receiving various operations from an operator, the estimation result of an estimation that is made during an operation by the control unit 150 that is described later, or the like. The communication unit 130 is a Network Interface Card (NIC), or the like, and it performs a communication with other devices.

As illustrated in FIG. 1, the storage unit 140 includes an image-data storage unit 141 and an estimation-criterion storage unit 142. For example, the storage unit 140 is a hard disk, a semiconductor memory device, or the like, and it stores various types of information. The image-data storage unit 141 stores medical image data that is acquired from the medical-image diagnostic apparatus or the image storage apparatus via the communication unit 130 and that is the object for the computer-aided diagnosis. The estimation-criterion storage unit 142 stores the estimation criterion that is generated by the control unit 150 that is described later.

The control unit 150 is, for example, an electronic circuit, such as a central processing unit (CPU) or a micro processing unit (MPU), or an integrated circuit, such as an application specific integrated circuit (ASIC) or a field programmable gate array (FPGA), and it performs the overall control on the medical-image processing apparatus 100.

Furthermore, as illustrated in FIG. 1, the control unit 150 includes, for example, an image acquiring unit 151, a determining unit 152, a dividing unit 153, an extracting unit 154, and an estimating unit 155. Moreover, the control unit 150 determines a disease candidate region in the medical image data that is the object for the computer-aided diagnosis and estimates the disease state with regard to the determined disease candidate region. An explanation is given below of, for example, the case of benign/malignant differentiation of a lung nodule as the object for the computer-aided diagnosis.

The image acquiring unit 151 acquires medical image data, which is the object for the computer-aided diagnosis, from the undepicted medical-image diagnostic apparatus or the image storage apparatus, via the communication unit 130 and stores it in the image-data storage unit 141. For example, on the basis of the information that is input from an operator via the input unit 110, the image acquiring unit 151 acquires medical image data that is obtained by scanning a lung region, which is the object for the computer-aided diagnosis, from the medical-image diagnostic apparatus, such as an X-ray CT apparatus or an MRI apparatus, or the image storage apparatus and stores it in the image-data storage unit 141.

Figure 2:
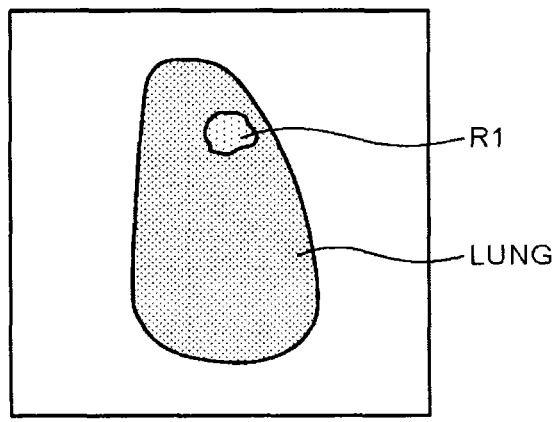
FIG. 2 is a diagram that illustrates an example of the operation performed by a determining unit according to the first embodiment.

The determining unit 152 determines a disease candidate region by using a predetermined medical image. Specifically, the determining unit 152 determines a disease candidate region that is included in the medical image data that is acquired by the image acquiring unit 151 and that is stored in the image-data storage unit 141. FIG. 2 is a diagram that illustrates an example of the operation performed by the determining unit 152 according to the first embodiment. For example, as illustrated in FIG. 2, the determining unit 152 determines a disease candidate region R1 that is included in the medical image data that is obtained by scanning a lung. Then, the determining unit 152 stores, in the storage unit 140, a binary image in which the determined disease candidate region R1 and the other regions (background regions) are represented by using different values (e.g., the image in which the disease candidate region is "1" and the background region is "0"), as a mask image for limiting the processing range.

Here, the determining unit 152 can determine the disease candidate region by using various techniques. For example, the determining unit 152 determines the disease candidate region R1 according to the region growing method on the basis of pixel values by using a single point that is designated by a doctor via the input unit 110 as a seed point. Furthermore, not only the above-described region growing method but also various general region segmentation methods may be applied to determination of a disease candidate region. For example, the determining unit 152 can determine the disease candidate region R1 by using other methods, e.g., various region segmentation algorithms, such as Grabcut. Furthermore, if a disease is present in an organ other than a lung and if the disease is large-sized and it deeply invades the periphery, or the like, it is assumed that the accuracy of the region segmentation algorithm of the determining unit 152 is insufficient; however, even in such a case, it is possible to determine, as the disease candidate region R1, the region that is set by a doctor via the input unit 110.

With reference back to FIG. 1, the dividing unit 153 divides the disease candidate region, which is included in medical image data and which is the object for the diagnosis, into multiple partial regions (sub regions). Specifically, the dividing unit 153 divides the disease candidate region that is determined by the determining unit 152 into multiple sub regions. For example, the dividing unit 153 divides the disease candidate region into multiple sub regions on the basis of the shape of the disease candidate region. Here, for example, with regard to the majority of malignant tumors, degeneration, necrosis, or the like, occurs inside the disease;

therefore, it is considered that it has different characteristics from those of the periphery of the disease. Thus, in the case of the computer-aided diagnosis for which, for example, a lung nodule is the target, the dividing unit 153 divides the disease candidate region into sub regions, i.e., the periphery and the inside.

Figure 3A:
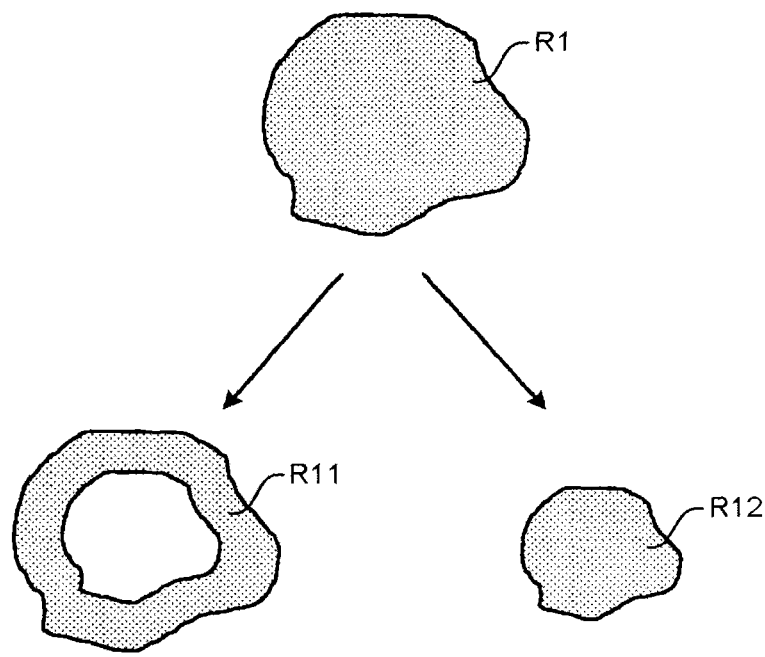
FIG. 3A is a diagram that illustrates an example of the operation performed by a dividing unit according to the first embodiment.
Figure 3B:
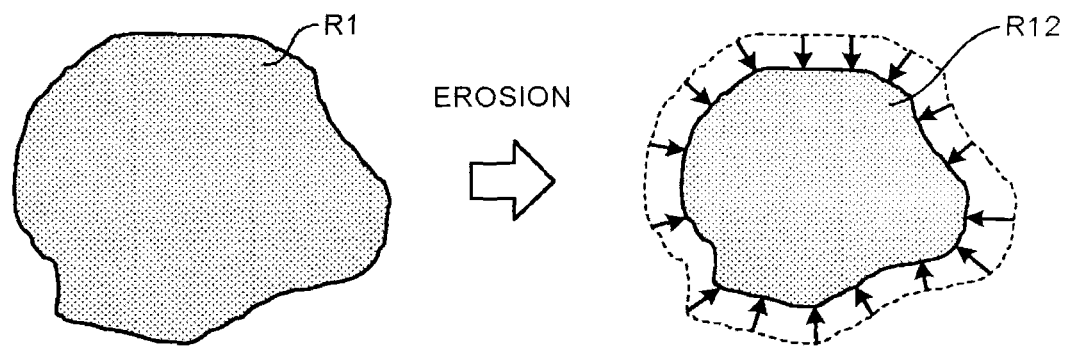
FIG. 3B is a diagram that illustrates an example of the operation performed by a dividing unit according to the first embodiment.

FIGS. 3A and 3B are diagrams that illustrate an example of the operation performed by the dividing unit 153 according to the first embodiment. For example, as illustrated in FIG. 3A, the dividing unit 153 divides the disease candidate region R1, which is determined by the determining unit 152, into a sub region R11 that is the periphery and into a sub region R12 that is the inside on the basis of the mask image that is stored in the storage unit 140. Here, for example, as illustrated in FIG. 3B, the dividing unit 153 applies morphological erosion to the mask image, which is a binary image, thereby separating the sub region R12, which is the inside, from the disease candidate region R1.

Specifically, with regard to each pixel of the disease candidate region R1 in the binary image, the dividing unit 153 replaces the value of the pixel that abuts the background region with the value of the background region (for example, replaces "1" with "0"), thereby extracting the sub region R12 that is the inside. Then, the dividing unit 153 subtracts the sub region R12 from the disease candidate region R1, thereby extracting the sub region R11 that is the periphery. Although the disease candidate region R1 is divided into the sub region R11 and the sub region R12 as described above, the dividing unit 153 here divides the disease candidate region R1 such that the sub region R11 and the sub region R12 constitute a predetermined percentage.

For example, the dividing unit 153 adjusts the number of times erosion is performed on the basis of the size of the disease candidate region R1, thereby dividing the disease candidate region R1 such that the sub region R11 and the sub region R12 constitute a predetermined percentage. The division percentage may be optionally set by an operator (a doctor, or the like), and there may be a case where it is set in accordance with, for example, the target disease. Although an explanation is given in FIGS. 3A and 3B of a case where the disease candidate region R1 is divided into two sub regions, there is no limitation on the embodiment, and there may be a case where the disease candidate region R1 is divided into, for example, three or more sub regions.

In such a case, the dividing unit 153 performs erosion to extract multiple regions with different sizes in a step-by-step manner and repeats a subtraction operation in a stepwise fashion to subtract the region with the size that is one step smaller from the region with the size that is one step larger, thereby dividing the disease candidate region into three or more sub regions. For example, the dividing unit 153 performs erosion to extract a sub region R13 that is smaller than the sub region R12 and subtracts the sub region R13 from the sub region R12, thereby separating the sub region that is one step outside the sub region R13 that is the inside.

Figure 4:
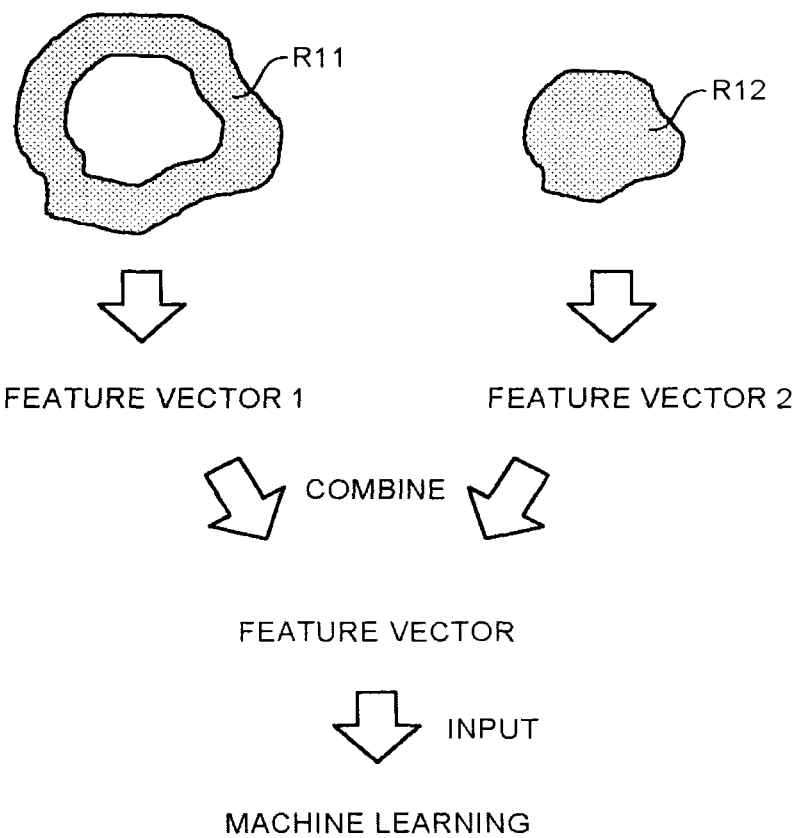
FIG. 4 is a diagram that illustrates an example of the operation performed by an extracting unit according to the first embodiment.

With reference back to FIG. 1, the extracting unit 154 extracts each of the feature values that correspond to the sub regions, which are divided by the dividing unit 153, as the feature value of the disease candidate region. Specifically, the extracting unit 154 combines the feature values of the sub regions to obtain the feature value of the disease candidate region. FIG. 4 is a diagram that illustrates an example of the operation performed by the extracting unit 154 according to the first embodiment. For example, as illustrated in FIG. 4, the extracting unit 154 determines the sub region R11 and the sub region R12 in the medical image data on the basis of the sub region R11 and the sub region R12 that are divided in the mask image and extracts a feature vector 1 of the determined sub region R11 and a feature vector 2 of the sub region R12. Then, the extracting unit 154 combines the extracted feature vector 1 and the feature vector 2 to extract the feature vector of the disease candidate region R1 and performs machine learning by using the extracted feature vector as an input.

Here, the extracting unit 154 can extract the feature vector of a sub region by using various techniques. For example, with respect to each of the divided sub regions, the extracting unit 154 can calculate the size, the degree of sphericity, the histogram of pixel values, various types of texture analysis, or the like, as the feature vector. Furthermore, with respect to each of the sub regions, the extracting unit 154 can use the above-describe calculated feature vector so as to calculate a feature vector using an intermediate representation, such as "bag of visual words", "fisher vector", or "sparse coding and max pooling". Here, the extracting unit 154 extracts the same type of feature vector with regard to each of the sub regions and combines the extracted feature vectors.

FIG. 5 is a diagram that illustrates an example of the operation performed by the extracting unit 154 to extract a feature vector according to the first embodiment. FIG. 5 illustrates a case where the histogram of pixel values is calculated as a feature vector. Furthermore, in the histogram of FIG. 5, the vertical axis represents the frequency, and the horizontal axis represents the feature vector element (dimension). For example, as illustrated in (A) of FIG. 5, the extracting unit 154 calculates the histogram of pixel values of the sub region R11 and the histogram of pixel values of the sub region R12. Specifically, as illustrated in (A) of FIG. 5, the extracting unit 154 calculates the histogram that is represented by using the feature vector "$a_1, \ldots, a_n$" in which the number of elements is "n" as the feature value of the sub region R11. In the same manner, as illustrated in (A) of FIG. 5, the extracting unit 154 calculates the histogram that is represented by using the feature vector "$b_1, \ldots, b_m$" in which the number of elements is "m" as the feature value of the sub region R12. The number of elements "n" and "m" may be the same number or may be different numbers. Then, as illustrated in (B) of FIG. 5, the extracting unit 154 combines the calculated histograms to extract the feature vector of the disease candidate region R1. Specifically, as illustrated in (B) of FIG. 5, the extracting unit 154 concatenates the feature vector "$a_1, \ldots, a_n$", in which the number of elements is "n", and the feature vector "$b_1, \ldots, b_m$", in which the number of elements is "m", thereby extracting, as the feature value of the disease candidate region R1, "the feature vector '$a_1, \ldots, a_n, b_1, \ldots, b_m$'" in which the number of elements is "n+m".

As the feature vectors are concatenated as described above, the feature vector of the disease candidate region R1, which is extracted by the extracting unit 154 according to the first embodiment, includes the information on the histograms of the sub region R11 and the sub region R12, as illustrated in (B) of FIG. 5. An explanation is given by using an example. If there are 256 pixel values of each of the sub region R11 and the sub region R12 (the number of elements "n=256" and the number of elements "m=256"), the 256-dimensional feature vector is obtained from the sub region R11, and the 256-dimensional feature vector is obtained from the sub region R12. Then, these feature vectors are concatenated so that the 512-dimensional feature vector that doubles (256+256) in length is extracted as illustrated in (B) of FIG. 5. Thus, it is possible to estimate the disease state of a disease candidate region more accurately. Specifically, unlike the 256-dimensional feature vector in a case where the number of pixel values of each of the sub region R11 and the sub region R12 is 256 and the histogram of the pixel values of the sub region R11 and the histogram of the pixel values of the sub region R12 are simply combined (in a case where the frequencies of the same pixel values in the two histograms are combined while the horizontal axis of the histogram of each sub region represents the pixel value), the feature vector according to the present embodiment allows the feature of the disease candidate region R1 to be represented by using the 512-dimensional feature vector, and the accuracy with which the disease state is estimated can be improved. The example illustrated in FIG. 5 is only an example, and there is no limitation on the embodiment. Specifically, with regard to other than the histogram, the extracting unit 154 can calculate the feature value and combine all the calculated feature values, thereby extracting the feature vector of the disease candidate region R1.

After the extracting unit 154 extracts the feature vector of the disease candidate region R1, the estimating unit 155 performs machine learning by using the extracted feature vector as an input. Here, the estimating unit 155 has two major functions, i.e., the one is to estimate the disease state of an unknown disease of which the disease state is not known, and the other is to generate the estimation criterion for making estimation. In either case, the estimating unit 155 needs the feature vector that is extracted by the extracting unit 154. For generation of an estimation criterion, the estimating unit 155 uses the extracted feature vector to generate an estimation criterion for a computer-aided diagnosis and stores the generated estimation criterion in the estimation-criterion storage unit 142. For example, the estimating unit 155 uses the support vector machine (SVM) technique to generate a classifier (classification of whether it is benign or malignant) for benign/malignant differentiation of a lung nodule.

In such a case, for example, the extracting unit 154 first extracts the feature vector of the lung nodule region from each of the supervised images in which it is determined whether the extracted lung nodule is benign or malignant as described above, uses the feature vector to generate a classifier with which the estimating unit 155 classifies benignancy and malignancy, and stores it in the estimation-criterion storage unit 142. Here, each time the feature vector of a disease candidate region is extracted from medical image data, the estimating unit 155 receives a determination result as to whether the corresponding lung nodule is benign or malignant from a doctor, or the like, via the input unit 110.

Then, the estimating unit 155 uses the extracted feature vector and the received determination result to update the classifier that is stored in the estimation-criterion storage unit 142. Thus, each time the extracting unit 154 extracts the feature vector of a disease candidate region, the estimating unit 155 updates the classifier; thus, it is possible to generate a classifier with a higher accuracy. Furthermore, the classifier stored in the estimation-criterion storage unit 142 is, for example, a linear function with the number of dimensions that constitute the feature vector; however, other discriminant functions may be used. Furthermore, not only the above-described SVM technique but also various different generally-used machine learning techniques may be applies to the machine learning of the estimating unit 155. Furthermore, in the explanations of the above-described example, each time the feature vector of a disease candidate region in medical image data is extracted, a determination result as to whether a corresponding lung nodule is benign or malignant is received from a doctor. However, there is no limitation on the embodiment, and there may be a case where, for example, the estimation result made by the estimating unit 155 is used as described later.

For estimation of the disease state, the estimating unit 155 uses the feature value of the disease candidate region that is extracted by the extracting unit 154 to estimate the disease state of the disease candidate region. Specifically, the estimating unit 155 estimates the disease state of the disease candidate region for which the extracting unit 154 extracts the feature vector on the basis of the estimation criterion that is stored in the estimation-criterion storage unit 142. Here, the estimating unit 155 uses the classifier that is stored in the estimation-criterion storage unit 142 to estimate whether the lung nodule of the disease candidate region for which the feature vector is extracted is benign or malignant.

Figure 6:
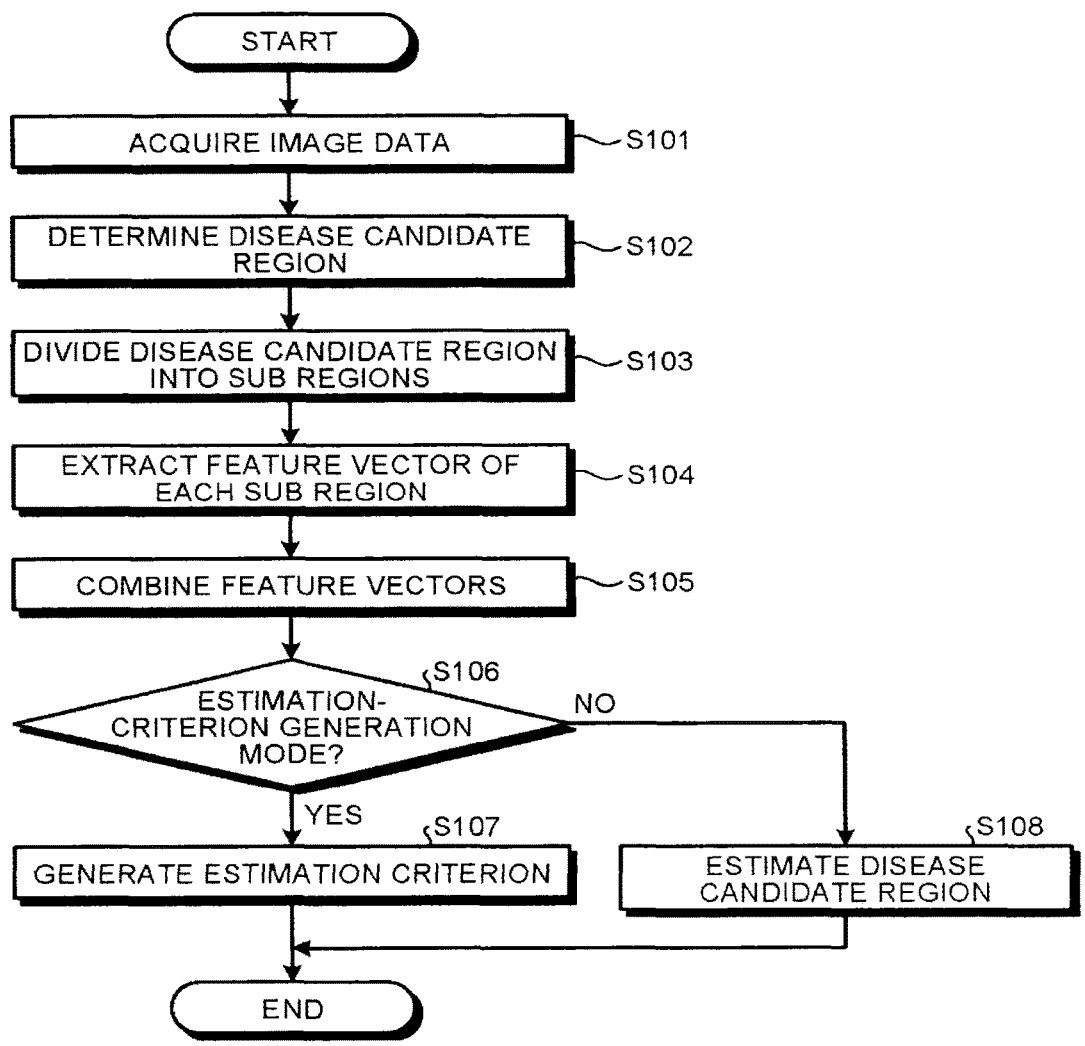
FIG. 6 is a flowchart that illustrates the steps of an operation of the medical-image processing apparatus according to the first embodiment.

FIG. 6 is a flowchart that illustrates the steps of an operation of the medical-image processing apparatus 100 according to the first embodiment. FIG. 6 illustrates an operation in a case where there are an estimation-criterion generation mode for generating an estimation criterion and an estimation mode for estimating the disease state of a disease candidate region.

As illustrated in FIG. 6, in the medical-image processing apparatus 100 according to the first embodiment, the image acquiring unit 151 acquires medical image data from the medical-image diagnostic apparatus or the image storage apparatus via the communication unit 130 (Step S101). Then, the determining unit 152 determines a disease candidate region in the acquired medical image data (Step S102).

Afterward, the dividing unit 153 divides the determined disease candidate region into multiple sub regions (Step S103), and the extracting unit 154 extracts a feature vector of each of the divided sub regions (Step S104). Then, the extracting unit 154 combines the feature vectors that are extracted from the sub regions (Step S105) to obtain the feature vector of the disease candidate region.

Afterward, the estimating unit 155 determines whether the estimation-criterion generation mode is set (Step S106). Here, if the estimation-criterion generation mode is set (Step S106, Yes), the extracting unit 154 receives a determination result of the estimating unit 155 and uses the received determination result and the feature vector to generate (update) the estimation criterion (Step S107). Conversely, if the estimation-criterion generation mode is not set (Step S106, No), the estimating unit 155 uses the estimation criterion stored in the estimation-criterion storage unit 142 to estimate the disease state of the disease candidate region (Step S108).

In the above-described operation example, an explanation is given of a case where the medical-image processing apparatus 100 processes a supervised image during the estimation-criterion generation mode (what is called, supervised learning). However, the estimation criterion may be updated by using the estimation result of an estimation by the estimating unit 155 using a non-supervised image (what is called, non-supervised learning or semi-supervised learning). In such a case, after the feature vectors are combined, the disease state of the disease candidate region is estimated, and the estimation criterion is generated (updated) by using the estimation result.

As described above, according to the first embodiment, the dividing unit 153 divides the disease candidate region, which is the object for the diagnosis and which is included in the medical image, into multiple sub regions. The extracting unit 154 extracts the feature value of each of the sub regions, which are divided by the dividing unit 153, as the feature value of the disease candidate region. Therefore, the medical-image processing apparatus 100 according to the first embodiment is capable of representing the feature vector of the disease candidate region by using multiple feature vectors of sub regions, thereby improving the diagnosis performance of a computer-aided diagnosis.

For example, for benign/malignant differentiation of a lung nodule, the medical-image processing apparatus 100 makes it possible to reflect the features in the case of a malignant tumor or in the case of a benign tumor by using the feature value, thereby improving the performance of a computer-aided diagnosis for benign/malignant differentiation of a lung nodule.

Furthermore, according to the first embodiment, the extracting unit 154 combines the feature values of multiple sub regions to obtain the feature value of the disease candidate region. Therefore, the medical-image processing apparatus 100 according to the first embodiment is capable of representing the feature of a single disease candidate region by using a single feature vector and easily performing various types of machine learning.

Furthermore, according to the first embodiment, the dividing unit 153 divides the disease candidate region into multiple sub regions on the basis of the shape of the disease candidate region. Therefore, the medical-image processing apparatus 100 according to the first embodiment is capable of easily dividing the inside and the periphery of a disease candidate region.

Furthermore, according to the first embodiment, the estimating unit 155 estimates the disease state of a disease candidate region on the basis of the feature value of the disease candidate region that is extracted by the extracting unit 154. Therefore, the medical-image processing apparatus 100 according to the first embodiment can make an estimation with a higher accuracy.

Second Embodiment

According to the above-described first embodiment, an explanation is given of a case where a disease candidate region is divided into sub regions on the basis of the shape of the disease candidate region. According to a second embodiment, an explanation is given of a case where a disease candidate region is divided into sub regions on the basis of the pixel value of medical image data. The medical-image processing apparatus 100 according to the second embodiment is different from the medical-image processing apparatus 100 according to the first embodiment in the details of the operation of the dividing unit 153. An explanation is primarily given below with reference to this aspect, the same reference marks as those in FIG. 1 are used for the components that have the same functions as those in the configuration that is described in the first embodiment, and their explanations are omitted.

For an image inspection using medical images, a single pixel of the image sometimes has a characteristic meaning. For example, in the CT, equal to or less than the pixel value (CT value) "−1000 HU" is equivalent to air, and "−100 HU" is equivalent to fat. Furthermore, for example, a high signal of a T2-weighted image of the MRI represents a liquid, and a high signal of a diffusion-weighted image represents a high cellular density. Furthermore, for example, in the FDG-PET, the area with a high pixel value is the region with high sugar metabolism.

Figure 7:
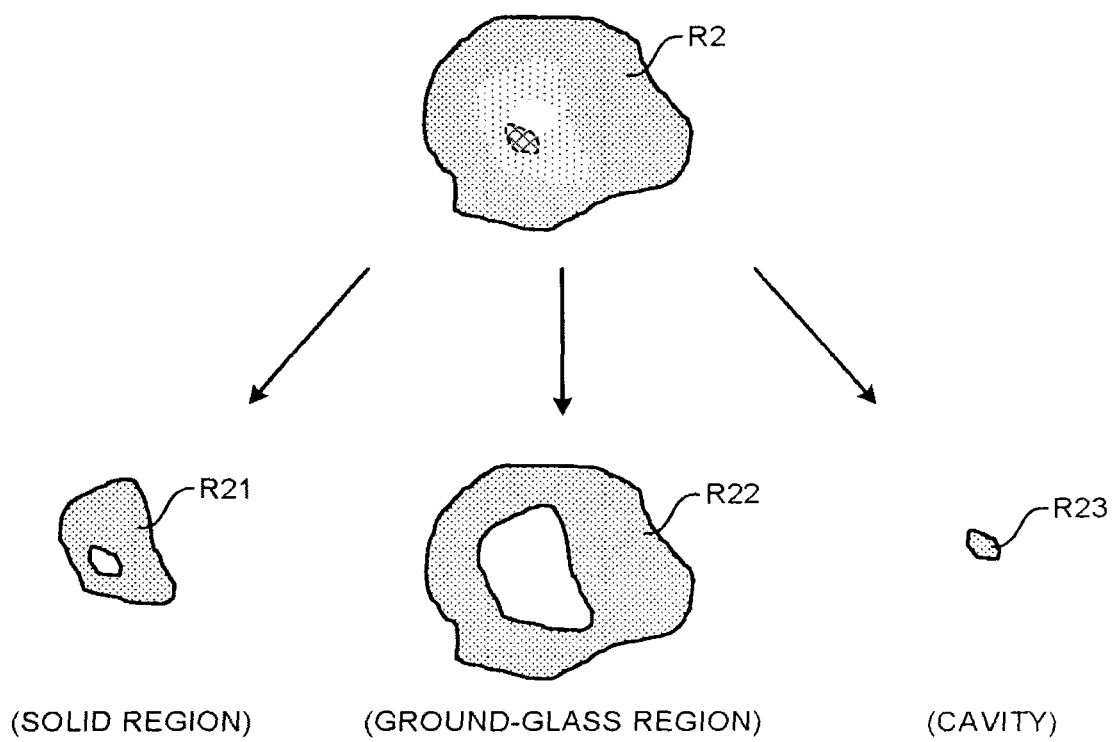
FIG. 7 is a diagram that illustrates an example of the operation performed by the dividing unit according to the second embodiment.

It is considered that the above characteristic pixel value is sometimes present with regard to the inside of the disease. Therefore, the dividing unit 153 according to the second embodiment divides a disease candidate region into multiple sub regions on the basis of the pixel value of the disease candidate region. FIG. 7 is a diagram that illustrates an example of the operation performed by the dividing unit 153 according to the second embodiment. An explanation is given in FIG. 7 of a case where a disease candidate region R2, which is determined in the CT image that includes a lung nodule, is divided by using a pixel value (CT value).

Opacities of a lung nodule principally include the solid type, ground-glass type, and cavity, and these opacities are sometimes mixed in a single lung nodule. Therefore, multiple thresholds for classifying them are previously set, and a disease candidate region is divided into multiple sub regions on the basis of the thresholds. Specifically, the dividing unit 153 divides the disease candidate region R2 into a sub region R21, a sub region R22, and a sub region R23 as illustrated in FIG. 7 in accordance with the predetermined threshold that is previously set for CT values. With regard to each sub region in the case of a lung nodule, the sub region R21 is a solid region, the sub region R22 is a ground-glass region, and the sub region R23 is a cavity, as illustrated in FIG. 7. Furthermore, in the case of the above-described example, the regions with higher CT values are determined as the solid region, the ground-glass region, and the cavity in descending order.

As described above, the dividing unit 153 divides a disease candidate region into sub regions in accordance with the pixel value that has a characteristic meaning in medical image data. The example illustrated in FIG. 7 is only an example, and there is no limitation on the embodiment.

After the dividing unit 153 divides the disease candidate region R2 into the sub regions R21 to R23, the extracting unit 154 extracts the feature vector with respect to each of the sub regions R21 to R23 and combines the three feature vectors to obtain the feature vector of the disease candidate region R2. Then, the estimating unit 155 uses the feature vector of the disease candidate region R2 to update the estimation criterion. Alternatively, the estimating unit 155 uses the feature vector of the disease candidate region R2 to estimate the disease state of the disease candidate region R2.

As described above, according to the second embodiment, the dividing unit 153 divides a disease candidate region into multiple sub regions in accordance with the pixel value of the disease candidate region. Thus, the medical-image processing apparatus 100 according to the second embodiment extracts a feature vector from the region that indicates the characteristic pixel value in the disease candidate region and from the other regions to obtain the feature vector of the disease candidate region, thereby making it possible to improve the diagnosis performance of the computer-aided diagnosis.

Third Embodiment

In the above-described first embodiment, an explanation is given of a case where a disease candidate region is divided into sub regions on the basis of the shape of the disease candidate region. Furthermore, in the second embodiment, an explanation is given of a case where a disease candidate region is divided into sub regions on the basis of the pixel value of medical image data. In a third embodiment, an explanation is given of a case where a disease candidate region is divided into sub regions on the basis of the shape of the disease candidate region and the pixel value of the medical image data. The medical-image processing apparatus 100 according to the third embodiment is different from the medical-image processing apparatus 100 according to the first embodiment and the second embodiment in the details of the operation of the dividing unit 153. An explanation is primarily given below with reference to this aspect, the same reference marks as those in FIG. 1 are used for the components that have the same functions as those in the configuration that is described in the first embodiment, and their explanations are omitted.

The dividing unit 153 according to the third embodiment divides a disease candidate region into multiple sub regions on the basis of the shape of the disease candidate region and the pixel value. For example, the dividing unit 153 divides a disease candidate region, which is determined by the determining unit 152, into multiple sub regions by using mean shift, Simple Linear Iterative Clustering (SLIC), or the like. For region division using the mean shift, for example, the dividing unit 153 uses a single pixel included in the disease candidate region as the initial point and performs the mean shift by using the area with a predetermined shape (e.g., a circle) and the pixel values of the pixels included in the area so as to acquire the convergence point that corresponds to the initial point. Then, the dividing unit 153 performs the mean shift by using, as the initial point, all the pixels included in the disease candidate region, thereby acquiring each convergence point.

After performing the mean shift by using all the pixels included in the disease candidate region as the initial point and acquiring each convergence point, the dividing unit 153 groups the convergence points on the basis of the pixel value of the convergence point, the distance between the convergence points, or the like. Then, the dividing unit 153 determines that the set of pixels at the initial points that correspond to the convergence points included in each group is a single sub region, thereby dividing the disease candidate region into multiple sub regions. Here, the number of groups for grouping the convergence points is set so that the number of sub regions is set.

Furthermore, in the case of region division using SLIC, the dividing unit 153 generates Superpixel on the basis of the pixel value of each pixel included in the disease candidate region so as to divide the disease candidate region into multiple sub regions. Here, the dividing unit 153 limits the search region for generating Superpixel in proportion to the size of Superpixel, thereby increasing the processing speed. Here, the shape or the size of the search region is changed so that the number of sub regions is set.

As described above, according to the third embodiment, the dividing unit 153 divides a disease candidate region into multiple sub regions in accordance with the shape of the disease candidate region and the pixel value. Therefore, the medical-image processing apparatus 100 according to the third embodiment can improve the accuracy with which a disease candidate region is divided into sub regions.

Fourth Embodiment

Heretofore, the first embodiment to the third embodiment are explained; however, various different embodiments may be implemented other than the first embodiment to the third embodiment that are described above.

In the first embodiment to the third embodiment that are described above, an explanation is given of a case where the feature vectors of sub regions are combined. However, there is no limitation on the embodiment and, for example, there may be a case where the feature vector of each sub region is used without being combined. In such a case, for example, the extracting unit 154 uses the feature vector of each sub region to generate an estimation criterion.

In the first embodiment to the third embodiment that are described above, an explanation is given of, for example, a case where two-dimensional medical image data is used. However, there is no limitation on the embodiment and, for example, there may be a case where medical image data that is high-dimensional data in three or more dimensions or multiple medical image data sets are used. In the case of, for example, three-dimensional data, the determining unit 152 determines a three-dimensional disease candidate region by using an area expansion technique using voxel values. Then, for example, the dividing unit 153 divides it into multiple three-dimensional sub regions on the basis of the shape of the disease candidate region or the voxel values. The extracting unit 154 extracts the feature vector of each of the divided three-dimensional sub regions and combines them, and the estimating unit 155 generates an estimation criterion and estimates the disease state of the three-dimensional disease candidate region on the basis of the combined feature vector.

Furthermore, if multiple medical image data sets are used, the determining unit 152 determines a disease candidate region by using a predetermined medical image, and the dividing unit 153 divides, into multiple sub regions, a disease candidate region in at least any one of the predetermined medical image and the other medical images. Here, if multiple medical image data sets are used, the following operation is performed. For example, the determining unit 152 determines a first disease candidate region in a first medical image, and the dividing unit 153 divides the first disease candidate region in the first medical image into multiple sub regions. Then, the extracting unit 154 applies the sub regions into a second medical image, calculates the feature values of the sub regions in the second medical image, and combines them so as to extract the feature value of the disease candidate region.

Furthermore, for example, the determining unit 152 determines the first disease candidate region in the first medical image. Then, the dividing unit 153 applies the determined disease candidate region to the second medical image and divides the disease candidate region in the second medical image into multiple sub regions. The extracting unit 154 calculates the feature values of the divided sub regions in the second medical image and combines them so as to extract the feature value of the disease candidate region.

Furthermore, for example, the determining unit 152 determines the first disease candidate region in the first medical image, and the dividing unit 153 divides the first disease candidate region in the first medical image into multiple sub regions. Then, the extracting unit 154 applies the sub regions to the second medical image and a third medical image, calculates and combines the feature values of the sub regions in the second medical image so as to extract the feature value of the disease candidate region in the second medical image, and calculates and combines the feature values of the sub regions in the third medical image so as to extract the feature value of the disease candidate region in the third medical image.

The above-described example is only an example, and there is no limitation on the embodiment in a case where multiple medical image data sets are used. Specifically, there may be a case where an arbitrary image out of the multiple medical images is used to determine a disease candidate region, divide the disease candidate region into multiple sub regions, and calculate a feature value. Here, multiple medical image data sets include, for example, medical images that are captured at different times for the same patient, multiple frames of a moving image, or the like.

Furthermore, according to the first embodiment to the third embodiment that are described above, the feature values of multiple partial regions of a disease candidate region are combined; however, there is no limitation on the embodiment. For example, the feature value of the entire disease candidate region may be extracted, and the feature value of the entire disease candidate region may be combined with the feature values of multiple partial regions. In this case, the same feature value or different feature values may be used for the feature value of the entire disease candidate region or the feature value of multiple partial regions.

Figure 8:
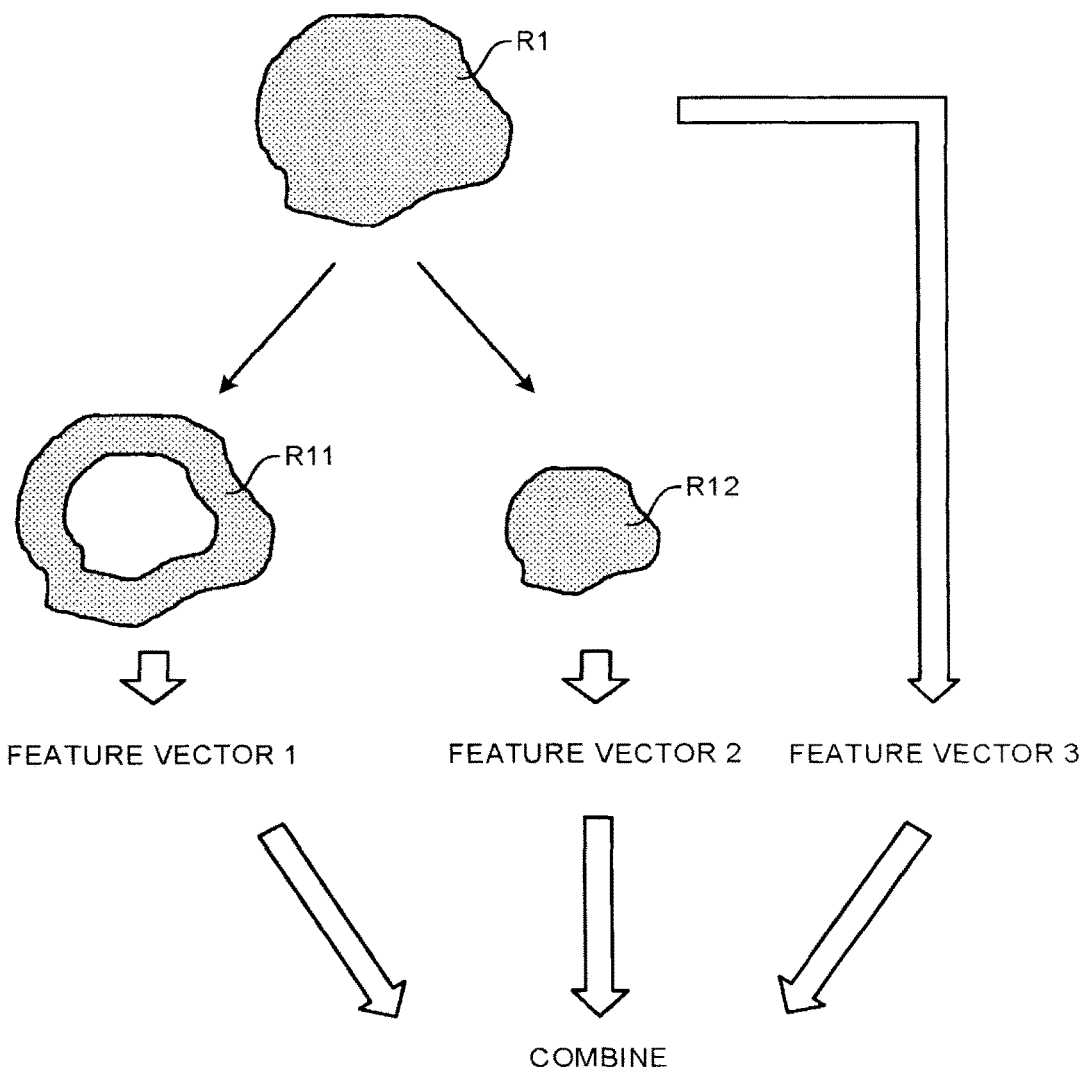
FIG. 8 is a diagram that illustrates an example of the operation that is performed by the extracting unit according to a fourth embodiment to extract a feature vector.

FIG. 8 is a diagram that illustrates an example of the operation that is performed by the extracting unit 154 according to a fourth embodiment to extract a feature vector. Here, FIG. 8 illustrates, for example, a case where the dividing unit 153 divides the disease candidate region R1, which is determined by the determining unit 152, into the sub region R11 and the sub region R12, and the extracting unit 154 combines the feature vectors of the disease candidate region R1, the sub region R11, and the sub region R12. For example, as illustrated in FIG. 8, the extracting unit 154 calculates an "n"-dimensional feature vector 1 of the sub region R11, an "m"-dimensional feature vector 2 of the sub region R12, and an "l"-dimensional feature vector 3 of the disease candidate region and calculates an "n+m+l"-dimensional feature vector by combining the calculated feature vectors. Furthermore, the extracting unit 154 is also referred to as a generating unit that generates the feature value of each of the partial regions and the feature value of the disease candidate region.

Then, the estimating unit 155 uses a combination of the feature value of each of the partial regions and the feature value of the disease candidate region to estimate the disease state of the disease candidate region. Specifically, the estimating unit 155 uses the feature value that is obtained by combining the feature values of the partial regions and the feature value of the disease candidate region to estimate the disease state of the disease candidate region. Specifically, the estimating unit 155 uses the "n+m+l"-dimensional feature vector, which is calculated by the extracting unit 154, as the feature value of the disease candidate region R1 to estimate the disease state of the disease candidate region R1. For example, the extracting unit 154 calculates the feature vector 1 of the sub region R11 and the feature vector 2 of the sub region R12 as the histogram of pixel values and calculates the feature vector 3 of the disease candidate region R1 as the shape, such as the cubic volume or the degree of sphericity. Then, the extracting unit 154 combines (concatenates) the feature vector 1, the feature vector 2, and the feature vector 3, and the estimating unit 155 estimates the disease state of the disease candidate region R1 by using the combined (concatenated) feature vectors. Thus, the medical-image processing apparatus 100 according to the present embodiment can estimate the disease state on the basis of the pixel values of sub regions included in the disease candidate region R1 and the shape of the disease candidate region R1, whereby the accuracy with which the disease state is estimated can be further improved.

Furthermore, in the first embodiment to the third embodiment that are described above, an explanation is given of a case where the image acquiring unit 151 acquires medical image data from the image storage apparatus or the medical-image diagnostic apparatus. However, there is no limitation on the embodiment, and there may be a case where, for example, a doctor carries medical image data by using a portable storage medium, such as a flash memory or an externally connected hard disk, and stores it in the image-data storage unit 141 of the medical-image processing apparatus 100. In such a case, acquisition of volume data may not be performed by the image acquiring unit 151.

Furthermore, in the first embodiment to the third embodiment that are described above, an explanation is given of the medical-image processing apparatus 100; however, there is no limitation on the embodiment, and there may be a case where, for example, the storage unit 140 and the control unit 150 of the medical-image processing apparatus 100 illustrated in FIG. 1 are installed in the medical-image diagnostic apparatus and the above-described operation is performed by the medical-image diagnostic apparatus.

Furthermore, the components of each apparatus illustrated in the above-described embodiment are functionally conceptual and do not necessarily need to be physically configured as illustrated in the drawings. Specifically, specific forms of separation and combination of each apparatus are not limited to those depicted in the drawings, and a configuration may be such that all or some of apparatuses are functionally or physically separated or combined in an arbitrary unit depending on various types of loads or usage. For example, there may be a case where determination of a disease candidate region, which is performed by the determining unit 152, is performed by the extracting unit 154. Moreover, all or any of various processing functions performed by each apparatus may be implemented by a CPU or a program that is analyzed and executed by the CPU or may be implemented as wired logic hardware.

With the medical-image processing apparatus according to at least one of the above-described embodiments, it is possible to improve the diagnosis performance of a computer-aided diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical-image processing apparatus comprising:
processing circuitry configured to:
extract a disease candidate region from a medical image;
divide the disease candidate region into an internal region and an external region, by performing erosion to the disease candidate region, the erosion being repeatedly performed so that a ratio between a size of the internal region and a size of the external region becomes a predetermined ratio;
extract a first feature vector of the internal region and a second feature vector of the external region;
generate a combining vector by combining the first feature vector and the second feature vector; and
estimate a disease state of the disease candidate region by using the combining vector,
wherein a number of elements of the combining vector is a total number of elements obtained by adding a number of elements of the first feature vector and a number of elements of the second feature vector
wherein the processing circuitry is configured to:
accept an estimation result in which a disease state of the disease candidate region is estimated; generate a classifier for a computer-aided diagnosis based on the combining vector and the estimation result; and estimate a disease state of a newly extracted disease candidate region by using the classifier.

2. The medical-image processing apparatus according to claim 1, wherein the processing circuitry is configured to:
   extract a third feature vector of disease candidate region before the dividing;
   generate a combining vector by combining the first feature vector, the second feature vector and the third feature vector; and
   estimate a disease state of the disease candidate region by using the combining vector,
   wherein a number of elements of the combining vector is a total number of elements obtained by adding a number of elements of the first feature vector, a number of elements of the second feature vector, and a number of elements of the third feature vector.

3. The medical-image processing apparatus according to claim 1, wherein the medical image is multiple medical image data sets.

* * * * *